United States Patent [19]

Kussick

[11] Patent Number: 5,779,470
[45] Date of Patent: Jul. 14, 1998

[54] TONGUE THRUST ORAL HABIT RETRAINER

[75] Inventor: Leon Kussick, Livingston, N.J.

[73] Assignee: Kussick Orthodontic Systems, LLC, Livingston, N.J.

[21] Appl. No.: 660,371

[22] Filed: Jun. 7, 1996

[51] Int. Cl.$^6$ .............................. A61C 3/00; A61F 5/56
[52] U.S. Cl. ........................... 433/6; 128/860; 128/861
[58] Field of Search ........................... 433/6; 128/848, 128/859, 860, 861, 862

[56] References Cited

U.S. PATENT DOCUMENTS

| | | | |
|---|---|---|---|
| 3,219,033 | 11/1965 | Wallshein | 128/136 |
| 3,277,892 | 10/1966 | Tepper | 128/172.1 |
| 3,286,576 | 11/1966 | West | 84/466 |
| 3,312,216 | 4/1967 | Wallshein | 128/136 |
| 3,334,417 | 8/1967 | Spengeman | 433/6 |
| 3,478,729 | 11/1969 | Tada | 123/117 |
| 3,478,742 | 11/1969 | Bohlmann | 128/172.1 |
| 3,510,946 | 5/1970 | Kesling | 32/14 |
| 3,522,805 | 8/1970 | Wallshein | 128/136 |
| 3,871,370 | 3/1975 | McDonald | 128/136 |
| 3,884,226 | 5/1975 | Tepper | 128/136 |
| 3,898,736 | 8/1975 | Bergersen | 32/14 B |
| 3,939,598 | 2/1976 | Bergersen | 32/14 B |
| 4,169,473 | 10/1979 | Samelson | 128/136 |
| 4,185,817 | 1/1980 | Peterson | 272/95 |
| 4,304,227 | 12/1981 | Samelson | 128/136 |
| 4,337,036 | 6/1982 | Hoffman | 433/5 |
| 4,504,225 | 3/1985 | Yoshii | 433/6 |
| 4,553,549 | 11/1985 | Pope et al. | 128/421 |
| 4,608,974 | 9/1986 | Sicurelli, Jr. | 128/136 |
| 4,718,662 | 1/1988 | North | 272/95 |
| 4,773,853 | 9/1988 | Kussick | 433/6 |
| 4,986,283 | 1/1991 | Tepper | 128/859 |
| 4,997,182 | 3/1991 | Kussick | 128/861 |
| 5,003,994 | 4/1991 | Cook | 128/848 |
| 5,018,533 | 5/1991 | Hawkins | 128/848 |
| 5,052,409 | 10/1991 | Tepper | 128/859 |
| 5,082,007 | 1/1992 | Adell | 128/860 |
| 5,092,346 | 3/1992 | Hays et al. | 128/848 |
| 5,133,740 | 7/1992 | Kussick | 606/236 |
| 5,316,020 | 5/1994 | Truffer | 128/848 |
| 5,467,783 | 11/1995 | Meade | 128/848 |

FOREIGN PATENT DOCUMENTS

WO 92/05752  4/1992  European Pat. Off. .

OTHER PUBLICATIONS

Dr. Leon Kussick, Bone Remodeling Orthodontics: An Early, One-Phase, Non-Extraction Therapy—Part II, *The Functional Orthodontist*, vol. 12, No. 1, pp. 4–15 (1995).

Dr. Leon Kussick, Bone Remodeling: The Next Generation of Orthodontics A Total, Early, Non-Extraction Approach, *The Functional Orthodontist*, Mar./Apr., pp. 1–8 (1985).

Dr. Robert M. Little et al., Stability and Relapse of Mandibular Anterior Alignment–First Premolar Extraction Cases Treated by Traditional Edgewise Orthodontics, *American Journal of Orthodontics*, vol. 80, No. 4, Oct. (1981).

E. A. Mitchell et al., Dummies and the Sudden Infant Death Syndrome, *Archives of Disease in Childhood*, 68:501–504 (1993).

James Woodford, How Sucking on Dummies May Save Your Baby's Life, Appeared in (Australia) *Sidney Morning Herald*, Aug. 19, 1993.

Snoring/Sleep Apnea Adjustable Appliance, Dental Products Report, pp. 89, Jun. 1996.

Silencer Therapy, Town & Country Dental Studios, undated.

*Primary Examiner*—Nicholas D. Lucchesi
*Attorney, Agent, or Firm*—Dechert, Price & Rhoads

[57] ABSTRACT

The invention relates to a tongue thrust habit oral corrective device designed to be retained by the posterior teeth and to train the tongue to avoid thrusting against the front teeth during swallowing, the device comprising: a teeth-fitting segment adapted to fit under at least the upper first posterior teeth; a palatal bridge extending from the teeth-fitting segment and adapted to avoid contacting the palate; and a downward projection adapted to create, with the teeth-fitting segment and the upper projection, a rearwardly opening pouch or channel in which the user's tongue is engulfed at a central location within the mouth so that the tip of the tongue is positioned properly and accurately for initiating a normal swallow.

22 Claims, 2 Drawing Sheets

TONGUE THRUST ORAL HABIT RETRAINER

The present invention relates to an oral corrective device for correcting tongue thrust problems associated with swallowing and other oral habits.

In normal swallowing, the tip of the tongue is first placed against the front of the palate or upper jaw just behind the front teeth. In swallowing, the tongue and its top surface is then moved upwards and backwards against the hard palate. People with tongue thrust problems (usually children) generally position the tongue too low in the mouth and too far forward at the start of a swallow which moves the tongue forward against, and in front of, the front upper teeth at the end of the swallow. The repeated pressure of the tongue thrust habit often displaces the upper front teeth and surrounding bone upwards and forwards, creating an open space between the upper and lower front teeth. This open space is called an anterior bite malocclusion. Most often, tongue thrusting patients also press their lower lips against the back of the upper front teeth during an incorrect and slow swallow, further aggravating the malocclusion.

The applicant has previously described a device for correcting tongue thrust problems in U.S. Pat. No. 4,997,182. The applicant has found this device to be effective to correct tongue thrust problems and facilitate the correction of malocclusions caused by incorrect swallowing and other oral habits. The device is believed to operate through stereotaxic conditioning, where the densely innervated surface of the tongue tip is trained to contact the densely innervated anterior bend of the hard palate located immediately behind the upper front teeth. This trained position is the correct position for initiating a normal swallow. The device of U.S. Pat. No. 4,997,182 needs improvement however, since it requires substantial skill and patience to correctly fit the device in a patient's mouth. Accordingly, features have been added to the basic tongue thrust corrective device of U.S. Pat. No. 4,997,182 to facilitate fitting the device to a patient's mouth. The entire disclosure of U.S. Pat. No. 4,997,182 is incorporated herein by reference.

SUMMARY OF THE INVENTION

The invention provides a first embodiment tongue thrust oral corrective device designed to be fitted to the upper posterior teeth and to train the user to correctly swallow without thrusting the tongue against the front teeth, the device comprising:
- a teeth-fitting segment comprising (1) a first occlusal trough adapted to fit under at least one, on one side of the user's mouth, of the posterior teeth, (2) a second occlusal trough adapted to fit under at least one, on the other side of the user's mouth, of the posterior teeth, and (3) a forward portion adapted to fit under at least two upper front teeth;
- a downward projection extending from the teeth-fitting segment and adapted to create a ramp for directing the tip of the user's tongue towards the soft tissue of the front anterior bend of the user's palate; and
- a palatal bridge having a loop shape that loops above the teeth-fitting segment and connects the first and second occlusal troughs, wherein the palatal bridge is adapted, in conjunction with the teeth-fitting segment and the downward projection, to create an opening allowing the user's tongue to contact the soft tissue of the front anterior bend of the user's palate.

The combination of the downward projection, the teeth-fitting segment and the palatal bridge form a rearwardly opening pouch or channel in which the tongue is engulfed. This embodiment allows the device to be stably positioned in the patient's mouth while the device is being fitted by creating a three point contact with the upper posterior teeth, on each side of the mouth, and the upper front teeth. After the device is tightly fitted to a patient's upper posterior teeth, the portion of the device that allows contact with the upper incisal teeth is preferably cut or ground away before regular use of the device so that it does not interfere with the desirable downward and rearward drifting of the upper front teeth that occurs when they are relieved of repeated tongue thrust and lower lip pressure.

Preferably, the palatal bridge is adapted to avoid contacting the palate. Preferably, the downward projection is adapted to avoid applying pressure to the lower teeth or jaw when a patient closes his or her mouth. Preferably, each occlusal trough has a hole for anchoring a polymerizable material. Preferably, the holes have bevelled edges suitable for engaging the polymerizable material to facilitate bonding between the device and the polymerizable material. Preferably, the palatal bridge is adapted so that the top of the loop sits at a distance of from about 2 mm to about 4 mm from the palate. Preferably, the tongue thrust corrective device further comprises one or more lateral molding elevations from the teeth-fitting segment adapted to be fit in the patient's mouth in front of (i.e., to the cheek side of) at least about one of the posterior teeth. Preferably, the lateral molding elevations are adapted to avoid interfering with side access to the patient's upper six-year molars. Preferably, the tongue thrust corrective device further comprises at least one alignment projection adapted to be seated in front of the front teeth and a marker on the alignment projection at the median line of the device for aligning the device with either (1) the gap between the two front teeth, or (2) the center line of a patient's face.

The invention further provides a second embodiment tongue thrust oral corrective device designed to be fitted to the upper posterior teeth and to train the user to swallow without thrusting the tongue against the front teeth, the device comprising:
- a teeth-fitting segment comprising (1) a first occlusal trough adapted to fit under at least one, on one side of the user's mouth, of the posterior teeth, and (2) a second occlusal trough adapted to fit under at least one, on the other side of the user's mouth, of the posterior teeth;
- a downward projection extending from the teeth-fitting segment and adapted to create a ramp for directing the tip of the user's tongue towards the soft tissue of the front anterior bend of the user's palate;
- a palatal bridge having a loop shape looping above the teeth-fitting segment and connecting the first and second occlusal troughs, wherein the palatal bridge is adapted, in conjunction with the teeth-fitting segment and the downward projection, to create an opening allowing the user's tongue to contact the soft tissue of the front anterior bend of the user's palate; and
- one or more lateral molding elevations extending from the teeth-fitting segment adapted to fit in the patient's mouth to the outer or inner side of at least about one of the posterior teeth.

The corrective device of the invention is fitted to a patient's mouth by molding a polymerizable material onto the device and around the patient's posterior teeth and subsequently curing the material into a resilient solid that conforms to the shape of these teeth. To effectively seat the device around the patient's teeth, the shaped, cured material must conform to the shape of the outside surfaces of the patient's teeth and that shaped polymeric material must be strongly bonded to the device. The lateral molding elevations of the present invention allow the polymerizable material to be easily conformed to the shape of the outside surfaces of the fitted teeth. Since the lateral molding elevations are preformed when the device is manufactured, they provide a sturdy retaining wall for forming the moldings of the outer surfaces of the patient's teeth. The lateral molding elevations also provide important support and containment for the polymerizable material after it has been molded to the patient's teeth but before it has been cured. The preferred embodiments of the first embodiment apply to the second.

The invention further provides a third embodiment tongue thrust oral corrective device designed to be fitted to the upper posterior teeth and to train the user to swallow without thrusting the tongue against the front teeth, the device comprising:

- a teeth-fitting segment comprising (1) a first occlusal trough adapted to fit under at least one, on one side of the user's mouth, of the posterior teeth, and (2) a second occlusal trough adapted to fit under at least one, on the other side of the user's mouth, of the posterior teeth, wherein each occlusal trough has a hole for anchoring a polymerizable material;
- a downward projection extending from the teeth-fitting segment and adapted to create a ramp for directing the tip of the user's tongue towards the soft tissue of the front anterior bend of the user's palate; and
- a palatal bridge having a loop shape looping above the teeth-fitting segment and connecting the first and second occlusal troughs, wherein the palatal bridge is adapted, in conjunction with the teeth-fitting segment and the downward projection, to create an opening allowing the user's tongue to contact the soft tissue of the front anterior bend of the user's palate.

The holes of this embodiment facilitate bonding between the pre-formed device and the polymerizable material that is used to fit the device to a patient's mouth. Preferably, the holes have angled or bevelled edges to allow portions of the polymerizable material having greater diameter than the hole to be molded on both sides of the hole. These large diameter portions act as plugs or undercuts that stabilize the polymerizable material from separating from the pre-formed device. The preferred embodiments of the first embodiment apply to the third.

The invention further provides a method of fitting a tongue thrust corrective device comprising the steps of:

fitting the polymerizable material to the upper surface of the first and second occlusal troughs;

molding the polymerizable material to the shape of the upper teeth of a patient while visually aligning the centerline of the device with the centerline of the patient's teeth or mouth and assuring a stable three-point contact between teeth-fitting segment of the device and the upper front teeth and the posterior teeth on both sides of the mouth;

removing the device from the molded teeth; and curing the polymerizable material to increase its strength. Preferably, the method further comprises an initial partial curing following the fitting step and before the removing step. Preferably, the polymerizable material is a light-curable material and the curing comprises light curing. Preferably, the method further comprises sculpting the cured device to remove any portion of the device that contacts the upper front four teeth, with the sculpted device adapted to allow movement and eruption of the front teeth and adjustment to the local bone to correct open bite malocclusions caused by tongue thrust disorders.

DEFINITIONS

The following terms shall have the meaning set forth below:

occlusal surface of upper posterior (or buccal) teeth of the patient

The occlusal surface of upper posterior (or buccal) teeth of the patient is the chewing surface of the upper teeth located behind the canines.

molding walls or elevations

An exterior molding wall or elevation is an elevation on one side of a trough designed to contain and support the polymerizable material that will be molded to the shape of some of a patient's upper teeth. The elevations serve to support and facilitate shaping the polymerizable material to conform to the outer surfaces of the upper arch and teeth.

occlusal trough

An occlusal trough is a piece designed to facilitate molding of an appliance of the invention to the occlusal and side surface of the molars.

polymerizable material

A polymerizable material is any material that can be molded to conform to the shape of one or more teeth and subsequently cured to lock it into the molded shape.

posterior teeth

The posterior teeth are the teeth behind the canines; these teeth are sometimes called the buccal or cheek teeth.

DETAILED DESCRIPTION

Figure 1:
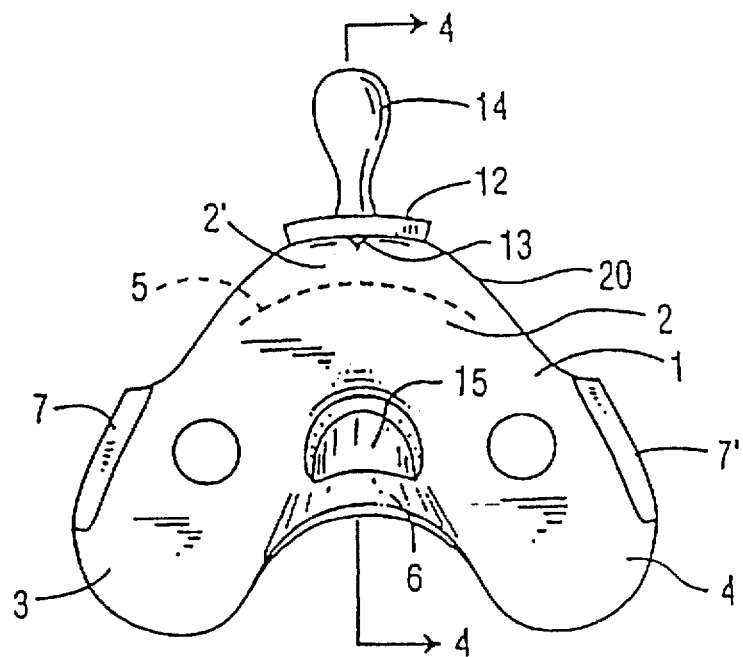
FIG. 1 displays an embodiment of the device
Figure 2:
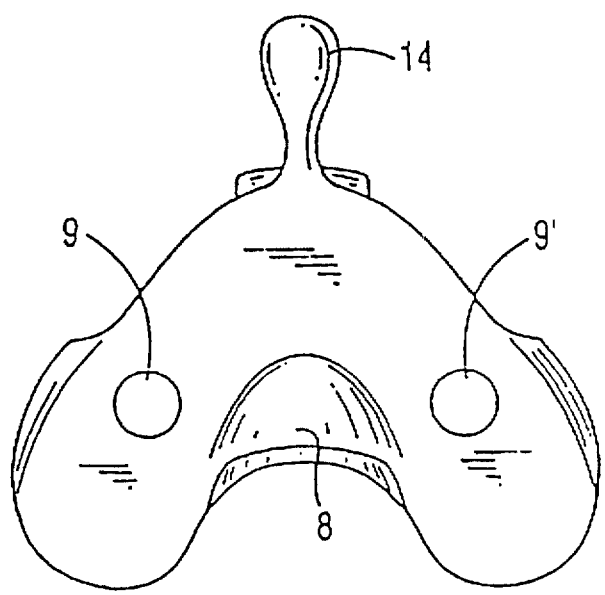
FIG. 2 displays a bottom view of an embodiment of the corrective device.

In FIG. 1, teeth-fitting segment 1 of device 20 is approximately semi-circular in shape and has a forward portion 2 and two rearward portions termed first occlusal trough 3 and second occlusal trough 4. Forward portion 2 is divided by reference line 5; that part of portion 2 in front of line 5, portion 2', will be cut or ground away after device 20 is fitted to the patient. Teeth-fitting segment 1 is sized to contact the upper posterior teeth at first occlusal trough 3 and second occlusal trough 4. Preferably, teeth-fitting segment 1 contacts at least one of the two upper posterior teeth on each side that are located immediately behind the canine tooth (i.e., the first and second molars). For children of less than about ten years of age, the teeth-fitting segment 1 will generally contact second baby molars; for older children and adults, teeth-fitting segment 1 will generally contact permanent bicuspids, i.e., premolars. Palatal bridge 6 forming the top of the tongue channel 11 (see FIG. 4) has a loop shape (channel visible in FIGS. 4 and 5). The top of palatal bridge 6 preferably seats about 2 mm to about 4 mm from the palate. First lateral molding elevation 7 and second lateral molding elevation 7' are adapted to seat beside the baby (i.e., deciduous) molars or permanent bicuspids of the user. Handle 14 can be used to aide the process of fitting and centering the device to a patient. As illustrated in FIGS. 1 and 2, most embodiments of the device will have two symmetrical halves. In FIG. 1, the device is symmetrical about the axis line indicating the cut-away view of FIG. 4.

Figure 3:
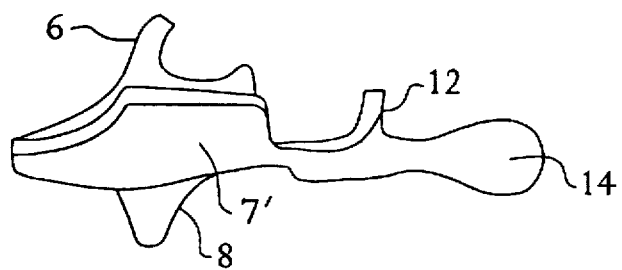
FIG. 3 displays a side view of an embodiment of the corrective device.

FIG. 2 displays a bottom view of an embodiment of the corrective device in which first hole 9 and second hole 9', which facilitate bonding of polymerizable material with the device, are visible. Downward projection 8 is visible in FIG. 2 and in FIG. 3, which shows a side view. Downward projection 8 forms the lower part of a channel or pouch in which the tongue fits. The channel 11 is shaped to direct the tip of the tongue to stretch upwards towards and contact the soft tissue of the front anterior bend of the user's palate FIG. 4 displays a cutaway along the central axis of symmetry of the displayed device, and in this view channel 11, which is formed from palatal bridge 6 and downward projection 8, and which directs the positioning of the user's tongue (30), is visible.

Figure 4:
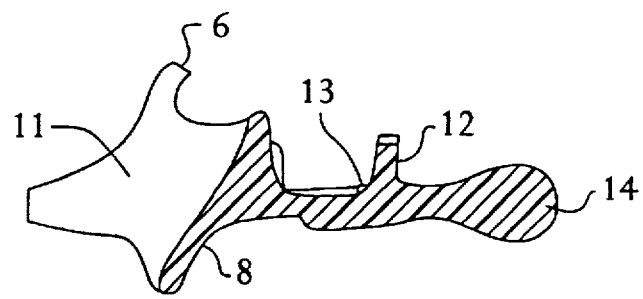
FIG. 4 displays a cutaway along the central axis of symmetry of the displayed device.
Figure 5:
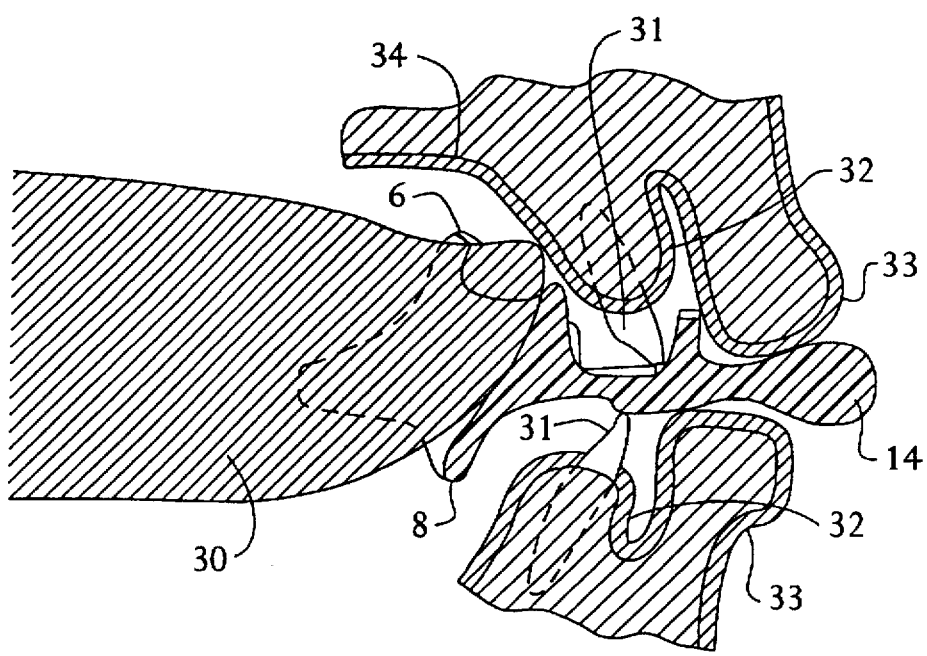
FIG. 5 displays the cutaway of FIG. 4 as it would seat in a patient's mouth during the fitting process.

FIG. 5 displays the cutaway of FIG. 4 as it would seat in a patient's mouth. Teeth 31, gums 32, lips 33 and palate 34 are also illustrated. The palatal bridge 6 defines a tongue hole 15 (see FIG. 1) to which the tongue is guided by channel 11 (see FIG. 4). Preferably, tongue hole 15 is sized so that the tongue has to stretch somewhat to contact the palate 34. When the tongue tip and the anterior bend of the palate just behind the front teeth are encouraged to contact each other, the sensory stimulus of both sensory-nerve rich structures is sufficiently rewarding as to encourage repeated further contact, thus rewarding the desired conduct of positioning the tongue at a position that is ideal for initiating a correct swallow.

The corrective device 20 can be manufactured in a wide range of sizes. However, a limited number of sizes should accommodate most patients. In fact, one universal size accommodates most children or adults older than four years of age. This embodiment is generally built to accommodate mouths having up to about 50 mm to about 55 mm separating the outer edges of the second baby molars or bicuspids. The corrective device 20 is constructed of a resilient solid plastic such as acrylic, including methacrylate, polycarbonate, such as Lexan (General Electric, Pittsfield, Mass.) polyarmomatic carbonate, or another polymer of comparable strength, biocompatability, moldability or bondability. It is preferably manufactured by injection molding.

The portion of the teeth-fitting segment 2 that rests under the upper incisal edges of the front teeth preferably includes a marking designating the center line of the device. The marking can be, among other things, a notch, crease, cavity, nob or a colored line. The marking can be an alignment projection 12 adapted to fit in front of the front teeth and having a protrusion 13 adapted to sit in the depression between the two front teeth (12 and 13 are visible in FIG. 4). Where the patient's front teeth do not adequately identify the center line of patient's mouth, facial markers such as the nose or chin may be used to visually align the device.

The teeth-fitting segment 1 is sufficiently planar to allow stable contact, on both sides of the patient's mouth, with the occlusal surface of upper posterior (or buccal) teeth of the patient. The portion 2' of the teeth-fitting segment 1 that fits under some or all of the upper front teeth is used to facilitate fitting the device to a patient. This forward subportion 2' creates a stabilizing third point of contact between the device and patient's upper front teeth, the other two points of contact being between (a) first occlusal trough 3 and the upper posterior teeth located on the patient's right side and (b) second occlusal trough 4 and the upper posterior teeth located on the patient's left side. After fitting, the forward subportion 2', which is not necessary for day-to-day use, is preferably cut away. Line 5 defining subportion 2' is selected to position, after subportion 2' is cut away, the front edge of the appliance parallel to and contoured to the arch shape of the upper front teeth. The first occlusal trough 3 and second occlusal trough 4 are used to support the polymerizable material that is molded to the shape of the patient's upper posterior teeth to snugly fit the device to the patient.

The teeth-fitting segment 1 preferably fits under at least two upper front teeth, more preferably at least four upper front teeth. The teeth-fitting segment will also fit under at least about one upper posterior tooth on each side of the mouth, preferably under at least about two such teeth on each side. After the polymerizable material is fitted to the device 20, the device will conform to the occlusal and side shape of these posterior teeth.

First lateral molding elevation 7 and second lateral molding elevation 7' preferably fit on the outer side (i.e., the cheek side) of at least one tooth on each side of the mouth. Preferably the first lateral molding elevation 7 and second lateral molding elevation 7' each fit to the outer side of two of the posterior teeth. In a preferred embodiment, first lateral molding elevation 7 and second lateral molding elevation 7' do not block side access to the first permanent molars (i.e., the "six-year" molars). This allows use of the six-year molars to anchor other orthodontic devices, such as a band, retaining arch wires or headgear devices for correcting overjets, for instance using buccal molar tubes attached to the six-year molars.

Generally, for narrow mouths, the lateral molding elevations can be ground away after they have been used to facilitate the molding of cured polymer around the patients' teeth. The removal of the extra material increases patient comfort while sufficient molded, cured polymerizable material remains to retain the upper posterior teeth.

First hole 9 and second hole 9' found in the teeth-fitting segment 1 of a preferred embodiment will generally have diameter from about 2 mm to about 8 mm, preferably from about 4 mm to about 6 mm. Generally, first hole 9 and second hole 9' will make up no more than about 30%, preferably 25%, more preferably 20%, of the total area of the teeth-fitting segment 1 that fits under the upper posterior teeth. First hole 9 and second hole 9' preferably have bevelled edges to facilitate bonding between the corrective device 20 and the polymerizable material used to fit the device to the patient's teeth. These larger diameter portions act as plugs or undercuts that stabilize the cured polymer from separating from the preformed corrective device 20. This bonding stabilization is particularly relevant during the process of molding polymerizable material to conform to the shape of a patient's teeth, at which point the bond between the appliance and the uncured or partially cured polymerizable material is generally weaker than it will be after further curing.

In a preferred embodiment of the corrective device 20, the palatal bridge 6 is adapted to avoid contacting the upper palate. In another preferred embodiment, the downward projection 8 is adapted to avoid hitting or applying pressure to the patient's lower teeth or jaw when the patient closes his jaws. Preferably, the downward projection 8 projects far enough to the back of the mouth to prevent the patient from biting behind the corrective device 20.

The corrective device 20 will be fitted to a patient's teeth or to a work model made from an impression of the patient's upper teeth and mouth using a polymerizable material which is preferably light curable, although other means of curing, such as for example heat curing, chemical curing and pressure curing, may be used. This material, prior to curing, should have a workable tack so that it can be manipulated yet will, at least for the short term, maintain a formed shape. A preferred polymerizable material is a urethanedimethacrylate material. Such a material is available as TRIAD VLC Provisional (rope form) from Densply of York, Pa. When TRIAD rope is used, preferably the appliance is wetted with a monomer solution such as the urethane-dimethacrylate monomer of the gel form of TRIAD VLC (Densply) or methyl methacrylate monomer (such as the solution sold as Orthodontic Resin, by the L. D. Cork division of Densply, Milford, Del., TRIAD VLC Bonding Agent from Densply, or SNAP liquid monomer from Parkell, Farmingdale, N.Y.) prior to applying the TRIAD rope material. Wetting with TRIAD VLC Bonding Agent can be conducted as recommended by the manufacturer, which recommended process includes (a) applying the Bonding Agent, (b) allowing the applied Bonding Agent to sit for one minute, and (c) exposing the applied Bonding Agent to a suitable light source for two minutes. The recommended process is believed to minimize the amount of methylmethacrylate monomer present.

The polymerizable material is fitted onto the upper surfaces of the teeth-fitting segment 1 that are to be fitted under and around the posterior teeth, specifically the first occlusal trough 3 and second occlusal trough 4. Preferably, the material will be firmly anchored to the corrective device by being plugged into first hole 9 and second hole 9' in the teeth-fitting segments. Preferably, some of the polymerizable material will be applied to the inner surfaces of the first lateral molding elevation 7 and second lateral molding elevation 7'.

While not illustrated, it should be recognized that the corrective device 20 can have a first inner lateral molding elevation 17 (not shown) and a second inner lateral molding elevation 17' (not shown). First lateral molding elevation 17 and second lateral molding elevation 17' seat to the inner side of the posterior teeth that fit into first occlusal trough 3 and the posterior teeth that fit into second occlusal trough 4, respectively, to support and contain the polymerizable material. First lateral molding elevation 7 and second lateral molding elevation 7' typically extend about 4 to about 8 mm above the floor—against which the posterior teeth seat—of the first occlusal trough 3 or second occlusal trough 4, respectively. First inner lateral molding elevation 17 and second inner lateral molding elevation 17' typically extend about 2 mm to about 3 mm above the floor of the first occlusal trough 3 or second occlusal trough 4, respectively.

The corrective device 20 is then fitted to the upper posterior teeth, taking care to visually align the device with the center line of the upper front teeth or mouth. The device and polymerizable material are then impressed onto the patient's posterior teeth or a model thereof, with the cusp tips contacting the floors of the occlusal troughs, while taking care that the forward portion 2 of the teeth-fitting segment 1 is centered and seated against the patient's upper front incisal edges. When the device 20 has first hole 9 and second hole 9', during this molding process, finger pressure can be applied to the polymerizable material extruding through the first hole 9 and second hole 9' to retain the polymerizable material and force it to flow around the surfaces of the patient's teeth, instead of further extruding through the first hole 9 and second hole 9'. Preferably, the polymerizable material is then partially cured as it sits engaged with the teeth. If the material is light curable, this may be done exposing the material to suitable light source, generally for 1 to 2 minutes. The corrective device 20 is then gently removed and further cured. Generally, when the polymer is light cured the additional curing is conducted for about 4 to about 6 minutes. After curing, any excess of the polymerizable material can be sculpted away.

After this curing and sculpting, on occassion the dental worker will find that the material conforming to some of the useful fitting surfaces of the patient's teeth have been removed. The fitting can be improved by creating a polymer with paste-like consistency in the teeth-conforming trough and again inserting the patient's teeth to cause the polymer paste to flow out over the useful fitting surfaces. Such a polymer paste can be self-curing (chemically) or can be curable by another method. For instance, the polymer paste can be TRIAD VLC gel or can be created by first applying Orthodontic Resin (L. D. Cork) and then adding SNAP self-cure resin (a quick-setting acrylic from Parkell Biomaterials Division, Farmingdale, N.Y.) to create a paste-like consistency. In the later case, repeated applications of the two components may be needed to create sufficient polymer paste. In fitting the polymer paste to a teeth model, a release material such as vasoline can be used to assure that the polymer paste does not bond to the model.

Forward portion 2 of teeth-fitting segment 1 is generally thicker than the floors of the first occlusal trough 3 and second occlusal trough 4. One reason for this thickness is the need for sufficient strength to support the grinding away of subportion 2'. Another reason is that in use the remaining part of forward portion 2 will contact the patient's front, lower incisors. The thinness of the first occlusal trough 3 and second occlusal trough 4 allows a more stable and even contact, when the patient bites, with the patient's lower front and posterior teeth. When these thinner portions contact the lower posterior teeth, the force imparted is evenly countered by the upper posterior teeth against which the thinner portions rest, allowing these portions to be thinner than forward portion 2 that encounters net torquing forces from contacting the lower front teeth. Generally, the teeth-fitting segment 1 fits under the second molars (i.e., the second tooth on each side behind the canines) and this portion of the teeth-fitting segment has a thickness of from about 1 mm and about 2 mm; and the portion that fits under the central two front teeth will preferably have a somewhat greater thickness adapted to allow for more even contact between the device and the patient's lower teeth. Such a greater thickness can be, for instance, about 3 mm to about 4 mm. An even bite or lower jaw closure happens when during a natural bite the lower teeth evenly contact the device 20 at three spaced points, with one such point of contact being with the front teeth, another being with posterior teeth on the right side, and the third being with posterior teeth on the left side.

If the corrective device 20 has a forward portion 2' of the teeth-fitting segment for forming the forward-most contact of a three point contact with the upper teeth during fitting, that portion is preferably cut away after the fitting process is complete. In a preferred embodiment, the corrective device 20 has an indentation in the teeth-fitting segment along a line defining the minimum amount of the forward part of the device that will be cut away after the device is fitted to a patient's mouth. The indentation facilitates an initial cutting away of the now unnecessary forward portion 2' of the corrective device 20. After this initial cutting, the device 20 can be further sculpted by grinding or cutting away the extra material.

The forward portion 2' of the teeth-fitting segment is preferably cut or ground away until the forward part of the corrective device (the remaining part of portion 2) seats in the patient's mouth from about 1 mm to about 3 mm, preferably about 2 mm, away from the position of the tips of the upper front teeth. In this way, the corrective device will not interfere with any downward and rearward drift of the teeth for their more ideal eruption, which corrective drift results from relief from the pressure caused by the tongue thrust habit. The sculpting preferably leaves a sufficient amount of forward portion 2 of the corrective device 20 positioned to block the patient from moving his or her lower lip up and behind his or her upper front teeth. With swallow retraining, which results in the upper front teeth drifting downwards and rearwards to a more ideal alignment, the device 20 can be further sculpted so that it does not interfere with the corrective drift and eruption of the upper front teeth.

The tongue thrust corrective device 20 is preferably worn at least about two to three hours a day (usually after school or after supper) and all night.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

I claim:

1. A pre-formed dental implement for forming therewith a tongue thrust habit oral corrective device, the implement designed to be fitted using a polymerizable material to the upper posterior teeth and to form the corrective device, which is utilized to train the user to swallow without thrusting the tongue or lower lip against the front teeth, the implement comprising:

a teeth-fitting segment comprising (1) a first occlusal trough adapted to fit under at least one, on one side of the user's mouth, of the posterior teeth, (2) a second occlusal trough adapted to fit under at least one, on the other side of the user's mouth, of the posterior teeth, and (3) a front portion adapted to fit under the upper front teeth, wherein the occlusal troughs facilitate molding the polymerizable material to the upper posterior teeth;

at least one alignment projection from the front portion adapted to be seated in front of the front teeth and a marker on the alignment projection at the median line of the device for aligning the device with either (a) the center of the two front teeth, or (b) the center line of a patient's face;

a downward projection extending from the teeth-fitting segment and adapted to create a ramp for directing the tip of the user's tongue towards the soft tissue of the front anterior bend of the user's palate; and a palatal bridge having a loop shape that loops above the teeth-fitting segment and connects the first and second occlusal troughs, wherein the palatal bridge is adapted, in conjunction with the teeth-fitting segment and the downward projection, to create an opening allowing the user's tongue to contact therethrough the soft tissue of the front anterior bend of the user's palate, wherein the front portion of the teeth-fitting segment and the alignment projection(s) are adapted to allow sculpting to assure that, after the fitting process, the corrective device does not contact the upper front teeth.

2. The pre-formed dental implement of claim 1, wherein the palatal bridge is adapted to avoid contacting the palate.

3. The pre-formed dental implement of claim 1, wherein the downward projection is adapted so as not to apply pressure to the lower teeth or jaw upon the patient's closing his or her mouth.

4. The pre-formed dental implement of claim 1, wherein each occlusal trough has a hole adapted for anchoring a polymerizable material.

5. The pre-formed dental implement of claim 1 comprising:

one or more lateral molding elevations extending from the teeth-fitting segment adapted to fit in the patient's mouth to the outer or inner side of at least about one of the posterior teeth and adapted to facilitate molding the polymerizable material to the upper posterior teeth.

6. The pre-formed dental implement of claim 5, wherein the lateral molding elevations are adapted to avoid blocking side access to the patient's upper six-year molars, thereby allowing these molars to anchor other orthodontic devices.

7. A method of fitting a tongue thrust habit corrective device formed of the pre-formed dental implement of claim 1, comprising the steps of:

placing the polymerizable material on the upper surface of the first and second occlusal troughs;

shaping the polymerizable material to the shape of the upper teeth of a patient while aligning the centerline of the implement with the centerline of the patient's mouth and assuring a stable three-point contact between teeth-fitting segment of the implement and the upper front teeth and the posterior teeth on both sides of the mouth;

removing the implement from the teeth; and curing the polymerizable material.

8. The method of fitting a tongue thrust habit corrective device of claim 7 comprising an initial partial curing after the shaping step but before the removing step.

9. The method of fitting a tongue thrust habit corrective device of claim 8, wherein said polymerizable material is a light-curable material and the curing comprises light curing.

10. The method of fitting a tongue thrust habit corrective device of claim 7 comprising sculpting the cured implement to remove any portion of the implement that contacts or restrains the upper front four teeth, the device formed by said sculpting being adapted to allow the natural movement and eruption of the upper front teeth and bone to correct open bite malocclusions caused by tongue thrust habit disorders.

11. The pre-formed dental implement of claim 1, further comprising, extending forward from the front portion a handle with an expanded knob adapted to facilitate manipulation of the implement by dental workers.

12. A pre-formed dental implement for forming therefrom a tongue thrust habit oral corrective device, the implement designed to be fitted using a polymerizable material to the upper posterior teeth and form the corrective device, which is utilized to train the user to swallow without thrusting the tongue against the front teeth, the implement comprising:

a teeth-fitting segment comprising (1) a first occlusal trough adapted to fit under at least one, on one side of the user's mouth, of the posterior teeth, and (2) a second occlusal trough adapted to fit under at least one, on the other side of the user's mouth, of the posterior teeth;

a downward projection extending from the teeth-fitting segment and adapted to create a ramp for directing the tip of the user's tongue towards the soft tissue of the front anterior bend of the user's palate;

a palatal bridge having a loop shape looping above the teeth-fitting segment and connecting the first and second occlusal troughs, wherein the palatal bridge is adapted, in conjunction with the teeth-fitting segment and the downward projection, to create an opening allowing the user's tongue to contact therethrough the soft tissue of the front anterior bend of the user's palate; and one or more lateral molding elevations extending from the teeth-fitting segment adapted to fit in the patient's mouth to the outer or inner side of at least about one of the posterior teeth and facilitate shaping the polymerizable material to the posterior teeth.

13. The pre-formed dental implement of claim 12 comprising a front portion with at least one alignment projection adapted to be seated in front of the front teeth and a marker on the alignment projection at the median line of the device for aligning the device with either (1) the center of the two front teeth, or (2) the center line of a patient's face.

14. The pre-formed dental implement of claim 12, wherein the one or more lateral molding elevations are adapted to seat to the outer or inner side of the posterior teeth.

15. The pre-formed dental implement of claim 14, wherein one or more lateral molding elevations are adapted to leave both upper six-year molars unblocked from the outer side and available for use to anchor another orthodontic appliance.

16. The pre-formed dental implement of claim 12, wherein the teeth-fitting segment further comprises a front portion adapted to fit under the upper front teeth.

17. The pre-formed dental implement of claim 16, wherein the front portion of the teeth-fitting segment is adapted to allow sculpting to assure that, after the fitting process, the corrective device does not contact the upper front teeth.

18. A method of fitting a tongue thrust habit corrective device formed of the pre-formed dental implement of claim 16, comprising the steps of:

placing the polymerizable material on the upper surface of the first and second occlusal troughs;

shaping the polymerizable material to the shape of the upper teeth of a patient while aligning the centerline of the implement with the centerline of the patient's mouth and assuring a stable three-point contact between teeth-fitting segment of the implement and the upper front teeth and the posterior teeth on both sides of the mouth;

removing the implement from the teeth; and curing the polymerizable material.

19. A pre-formed dental implement for forming therefrom a tongue thrust habit oral corrective device, the implement designed to be fitted to the upper posterior teeth and to form the corrective device, which is utilized to train the user to swallow without thrusting the tongue against the front teeth, the implement comprising:

a teeth-fitting segment comprising (1) a first occlusal trough adapted to fit under at least one, on one side of the user's mouth, of the posterior teeth, and (2) a second occlusal trough adapted to fit under at least one, on the other side of the user's mouth, of the posterior teeth, wherein each occlusal trough has a hole adapted for anchoring a polymerizable material;

a downward projection extending from the teeth-fitting segment and adapted to create a ramp for directing the tip of the user's tongue towards the soft tissue of the front anterior bend of the user's palate; and a palatal bridge having a loop shape looping above the teeth-fitting segment and connecting the first and second occlusal troughs, wherein the palatal bridge is adapted, in conjunction with the teeth-fitting segment and the downward projection, to create an opening allowing the user's tongue to contact the soft tissue of the front anterior bend of the user's palate.

20. The implement of claim 19, wherein the holes have bevelled edges to facilitate bonding between the implement and the polmerizable material.

21. A method of fitting a tongue thrust habit corrective device formed of the pre-formed implement of claim 19, comprising the steps of:

placing a polymerizable material on the upper surface of the first and second occlusal troughs;

shaping the polymerizable material to the shape of the upper teeth of a patient while aligning the centerline of the implement with the centerline of the patient's mouth and assuring a stable three-point contact between teeth-fitting segment of the implement and the upper front teeth and the posterior teeth on both sides of the mouth;

removing the implement from the teeth; and curing the polmerizable material.

22. The method of fitting a tongue thrust habit corrective device of claim 21 comprising an initial partial curing after the shaping step but before the removing step.

* * * * *